United States Patent
Clarke et al.

(10) Patent No.: US 7,095,555 B1
(45) Date of Patent: Aug. 22, 2006

(54) MULTIPLE PASS FARADAY ROTATION AMPLIFIER

(75) Inventors: Frederick W. Clarke, Madison, AL (US); Saulius Balevicius, Vilnius (LT)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/215,201

(22) Filed: Aug. 25, 2005

(51) Int. Cl.
*H01S 3/082* (2006.01)
(52) U.S. Cl. .......................... 359/347; 372/27; 372/97
(58) Field of Classification Search ................ 359/347; 372/27, 97
See application file for complete search history.

(56) References Cited

U.S. PATENT DOCUMENTS

| | | | |
|---|---|---|---|
| 4,328,468 A | 5/1982 | Krawczak et al. | |
| 4,909,612 A | 3/1990 | Scerbak et al. | |
| 5,268,787 A | 12/1993 | McIntyre | |
| 5,528,415 A | 6/1996 | Gauthier et al. | |
| 5,546,222 A | 8/1996 | Plaessmann et al. | |
| 5,982,174 A | 11/1999 | Wagreich et al. | |
| 6,384,966 B1 * | 5/2002 | Dymott | 359/347 |
| 2003/0133657 A1 | 7/2003 | Kochergin et al. | |
| 2004/0240031 A1 | 12/2004 | Azimi et al. | |

OTHER PUBLICATIONS

Brian J. Zook and Clifford R. Pollock, "Fiber Optic Tachometer Based on the Faraday Effect," *Applied Optics*, vol. 28, No. 11, Jun. 1, 1989, pp. 1991-1994.
Herbert Piller, "Faraday Rotation," in *Semiconductors and Semimetals*, eds. R. K. Willardson and A. C. Beer (Academic Press, New York, 1972), vol. 8, Ch. 3, pp. 103-179.

* cited by examiner

*Primary Examiner*—Mark Hellner
(74) *Attorney, Agent, or Firm*—USA Space and Missile Defense Command

(57) ABSTRACT

An apparatus for and a method of amplifying Faraday or Voigt rotation by passing light through a sample many times using multiple internal reflections and successive mirrored chambers that repeatedly send the light back through the sample. The sample is placed in a sample chamber that is adjacent to an optical amplifier chamber, and the optical amplifier chamber is adjacent to one or more additional chambers. The sample has a magnetic field applied thereto. The sample chamber receives light from a light source. The light reflects within the sample chamber and the sample to accumulate rotation of the light. The sample chamber transmits the light to the optical amplifier chamber. The optical amplifier chamber transmits the light to the additional chambers and reflects the light back to the sample where the light undergoes further rotation. Each one of the additional chambers transmits the light to the next additional chamber and reflects the light back to a previous chamber.

23 Claims, 2 Drawing Sheets

MULTIPLE PASS FARADAY ROTATION AMPLIFIER

BACKGROUND OF THE INVENTION

1. Field of the Invention

The present invention is directed, in general, to the amplification of Faraday or Voigt rotation and, more particularly, to the amplification of Faraday or Voigt rotation by passing a light beam through a sample of material many times through use of multiple internal reflections and successive mirrored chambers that repeatedly send the light beam back through the sample.

2. Description of the Related Art

Faraday rotation is the rotation of the plane of polarization of light as it passes through a material in the presence of a magnetic field, whose field lines are aligned with the direction of propagation of the light. Faraday rotation, $\theta$, is given by $\theta=VBL$, where V is a characteristic of the material referred to as the Verdet constant, B is the applied magnetic field strength, and L is the length of propagation of the light through the material (i.e., the thickness of the sample material).

Faraday rotation is a useful tool for examining semiconductors, but many modern semiconductor materials are single or multiple thin films. For example, modern mercury cadmium telluride (HgCdTe) infrared detector devices use thin films a few microns or nanometers in thickness on cadmium zinc telluride (CdZnTe) substrates. Faraday rotation is linearly dependent on material thickness, so very thin film materials often yield little or no Faraday rotation signal. Magnets currently available, even superconducting magnets, cannot make up for the lack of rotation signal in micron and even nanometer thick films. To obtain a usable Faraday rotation signal, current technology requires the thickness of a sample to be at least a few tenths of a millimeter for most materials. Thus, there is a need for amplification of Faraday rotation in thin film materials to allow screening of electrical properties that is non-destructive to the test sample, does not contaminate the test sample, and is faster and more easily automated.

Faraday rotation is a non-reciprocal effect in that it is not dependent on the direction of light through the sample. For example, for a DC magnet whose field lines are constant in one direction, if the plane of polarization of the light is rotated to the right with respect to a stationary observer as the light travels through the sample in one direction, it will rotate the same amount to the right if the light is redirected back through the sample, adding to the original rotation. If the light is sent back through the sample multiple times, the rotation will be multiplied by the number of paths the light takes through the sample. Thus, loss of signal rotation in even the thinnest films could be compensated for if the light could be directed through the sample thousands of times.

For further details concerning basic properties of Faraday rotation, refer to H. Piller, "Faraday Rotation," in *Semiconductors and Semimetals*, eds. R. K. Willardson and A. C. Beer (Academic Press, New York, 1972), vol. 8, Ch. 3, pp. 103–179. Also refer to B. J. Zook and C. R. Pollock, "Fiber Optic Tachometer Based on the Faraday Effect," *Applied Optics*, vol. 28, no. 11, June 1989, pp. 1991–1994, which describes doubling Faraday rotation in a simple device. These references are incorporated herein by reference to the extent necessary to make and practice the present invention.

SUMMARY OF THE INVENTION

To overcome the problem of little or no Faraday rotation being produced in thin film materials, the present invention amplifies Faraday rotation by generating many passes of light through a sample using multiple internal reflection and successive mirrored chambers that operate to repeatedly send the light back through the sample. Normally, multiple internal reflection is an undesirable effect that is avoided whenever possible in traditional Faraday rotation measurements due to an increase in rotation in low-absorbing, large Verdet constant materials, which is then corrected to yield accurate measurements. Here it is used to maximum effect where it is maximally occurring in a thin, low absorbing film to multiply (i.e., amplify) the Faraday rotation signal.

According to an embodiment of the present invention, a sample chamber is formed between an input and an output mirror with a sample placed between the mirrors. The sample is located between the poles of an electromagnet and is illuminated by an intense light source. Light traverses the sample chamber multiple times, undergoing cumulative Faraday rotation with each pass back and forth through the sample. The transparency of the input mirror is adjusted to allow sufficient light in from the source, while preventing the Faraday rotated light from escaping. The output mirror is adjusted to allow a maximum number of passes through the sample, in accordance with the absorption of the sample for the light frequency used, before the light is transmitted to the next chamber, which is an optical amplifier chamber. The light makes multiple passes in the optical amplifier chamber. Light intensity is adjusted via the optical gain of the chamber and the transparency of the optical amplifier chamber mirrors. Replenished light is then sent back to the sample chamber for another round of passes through the sample to accumulate further Faraday rotation. Successive chambers beyond the optical amplifier send light back through the optical amplifier and sample chambers to repeat the process and further multiply the Faraday rotation of the signal, so that even very thin film materials can be examined using Faraday rotation. The ultimate Faraday rotation amplification is determined by the number and transparency of the successive mirrored chambers.

It is an aspect of the present invention to provide an apparatus and method that enables the examination of thin film materials using Faraday rotation.

In another aspect of the present invention, there is provided an apparatus and method that increases the Faraday or Voigt rotation in thin film materials.

It is a further aspect of the present invention to provide an apparatus and method that multiplies Faraday or Voigt rotation by passing a light beam through a material multiple times.

It is yet another aspect of the present invention to provide an apparatus and method that uses a series of mirrored chambers to repeatedly send light back through a sample to accumulate Faraday or Voigt rotation in the sample.

To achieve the above and other aspects according to an embodiment of the present invention, there is provided a multiple pass light rotation amplifier. In the rotation amplifier, a sample chamber is defined by a first mirror and a second mirror and contains a sample surrounded by a magnetic field generator that creates a magnetic field around and through the sample. A light source supplies light to the sample chamber through the first mirror. The light reflects a plurality of times between the first mirror and the second mirror, and the light undergoes cumulative rotation of a plane of polarization of the light with each pass of the light through the sample. An optical amplifier chamber amplifies the light passing therethrough and is defined by the second mirror and a third mirror. The light reflects a plurality of times between the second mirror and the third mirror. One or more additional chambers are located beyond the optical amplifier chamber.

The sample chamber transmits the light to the optical amplifier chamber. The optical amplifier chamber transmits the light to a first one of the additional chambers and also transmits the light back to the sample where the light undergoes further rotation. Each one of the additional chambers transmits the light to a next one of the additional chambers and also transmits the light back to a preceding one of the additional chambers. The first one of the additional chambers transmits the light back to the optical amplifier chamber and a last one of the additional chambers outputs a rotation signal.

To achieve the above and other aspects according to another aspect of the present invention, there is provided a method of amplifying the rotation of a plane of polarization of light for a sample within a sample chamber. The sample chamber is adjacent to an optical amplifier chamber, and the optical amplifier chamber is adjacent to one or more additional chambers. Light is transmitted into the sample chamber and through the sample having a magnetic field applied thereto. The light reflects within the sample chamber and the sample to accumulate rotation of the plane of polarization of the light. The light is transmitted from the sample chamber to the optical amplifier chamber to amplify the light passing therethrough. The light is transmitted to a first one of the additional chambers and also reflected back to the sample where the light undergoes further rotation. The light is transmitted from the optical amplifier chamber to the additional chambers. Each one of the additional chambers transmits the light to a next one of the additional chambers and also reflects the light back to a previous one of the additional chambers. The first one of the additional chambers reflects the light back to the optical amplifier.

To achieve the above and other aspects according to yet another aspect of the present invention, there is provided a multiple pass light rotation amplifier having a sample chamber, an optical amplifier chamber, and a multiplier chamber. The sample chamber receives light from a light source and contains a sample of material to be examined. The light reflects a plurality of times within the sample and the sample chamber and undergoes cumulative Faraday rotation with each pass of the light through the sample. The optical amplifier is adjacent to the sample chamber and amplifies the light passing through this chamber. The multiplier chamber is adjacent to the optical amplifier chamber and receives the light from the optical amplifier chamber, outputs a rotation signal, and reflects the light back to the optical amplifier chamber. The optical amplifier chamber reflects the light received from the sample chamber and from the multiplier chamber back to the sample chamber, where the light undergoes further rotation.

The above and other aspects and advantages of the present invention, including various novel details of construction and combinations of parts and operations, will become apparent from the following description of the embodiments and the claims with reference to the accompanying drawings. The particular devices and operations embodying the invention are shown by way of illustration only and not as limitations of the invention. The principles and features of the present invention may be employed in various and numerous embodiments without departing from the scope of the invention.

BRIEF DESCRIPTION OF THE DRAWINGS

The present invention will now be described in detail with reference to the accompanying drawings, wherein like numerals refer to like parts throughout, and in which.

DETAILED DESCRIPTION OF THE PREFERRED EMBODIMENTS

Figure 1:
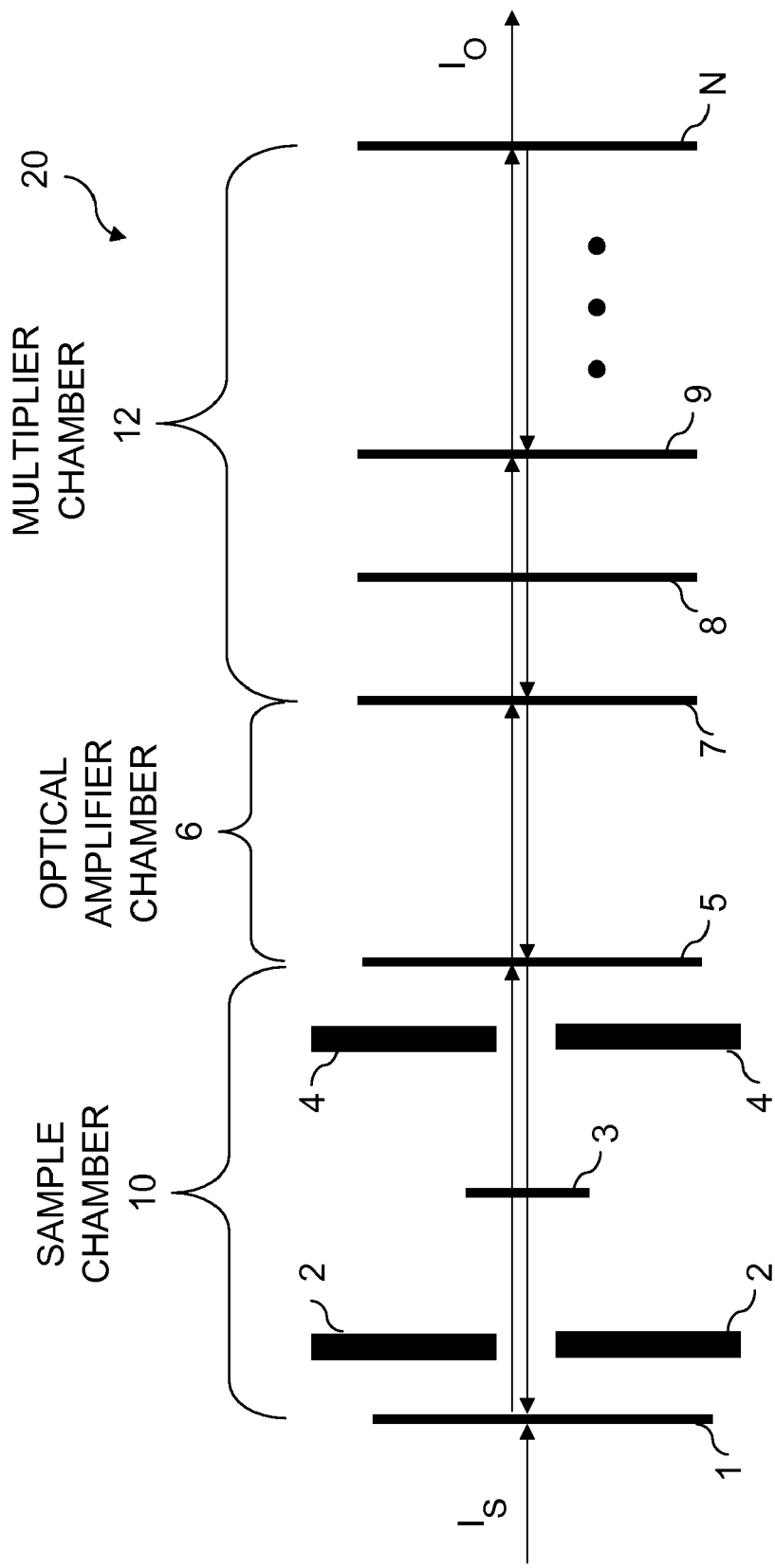
FIG. 1 shows a multiple pass Faraday rotation amplifier according to an embodiment of the present invention.

FIG. 1 shows a multiple pass Faraday rotation amplifier 20 according to an embodiment of the present invention. In FIG. 1, a light beam, having intensity $I_S$, from an intense light source (not shown), which can be either laser or incoherent light, passes through a partially transparent mirror 1 into a sample chamber 10. The light beam initially passes through a polarizer (not shown) between the light source and mirror 1 to produce linearly polarized light. The sample chamber 10 is formed by mirror 1 and another partially transparent mirror 5. The input mirror, mirror 1, allows light into the sample chamber 10 from the light source on the left, as viewed in FIG. 1, while preventing light approaching mirror 1 from the right from escaping the sample chamber 10. Mirror 1 is described in more detail below. The sample chamber 10 contains a sample 3 to be examined, which has polished front and back surfaces and is surrounded by an electromagnet having a first pole 2 and a second pole 4. The poles 2, 4 of the electromagnet are provided with holes to allow the light beam to pass through. The light beam that has passed through mirror 1 initially passes through the first pole 2 of the electromagnet.

After passing through the first pole 2 of the electromagnet, the beam contacts the sample 3. Part of the beam is reflected from the surface of the sample 3 back to mirror 1 and back again to the sample 3. The other part of the beam penetrates the sample 3 and undergoes multiple internal reflections between the front and back surfaces of the sample 3, accumulating one pass of Faraday rotation each time the beam is reflected back and forth, regardless of direction. The beam is slightly attenuated due to absorption by the sample 3. The beam then exits the sample 3, passes through the second pole 4 of the electromagnet, and contacts the output mirror, mirror 5, of the sample chamber 10. Because mirror 5 is partially transparent, part of the beam contacting mirror 5 is transmitted to an optical amplifier chamber 6 and part is reflected back to the sample 3. The reflected beam traveling back to the sample 3 from the right is partially transmitted through the sample 3, undergoing further multiple internal reflections (i.e., further accumulation of Faraday rotation), finally exits the sample 3, then is reflected back to the sample 3 by mirror 1 to repeat the process again.

The beam transmitted through the output mirror, mirror 5, of the sample chamber 10 passes into the optical amplifier chamber 6. The beam is amplified as it passes through the optical amplifier chamber 6 toward an output mirror, mirror 7, of the optical amplifier chamber 6. The beam is partially transmitted through mirror 7 into a multiplier chamber 12. The rest of the beam is reflected back at mirror 7 and travels back through the optical amplifier chamber 6. The beam makes several passes through the optical amplifier chamber 6, reflecting back and forth between mirrors 5 and 7. The amplification of the light intensity and number of passes of the light beam within the optical amplifier chamber 6 is determined by the optical gain of the optical amplifier chamber 6 and the transparency of the input mirror, mirror 5, and the output mirror, mirror 7. The multiplier chamber 12 contains a series of sub-chambers formed by additional mirrors 8, 9, . . . , N. The multiplier chamber 12 further multiplies the output Faraday rotation signal by repeatedly sending the light beam back through the optical amplifier chamber 6 and the sample 3. The light beam having intensity $I_O$ exits the Faraday rotation amplifier 20 and is passed to an analyzer (not shown) and then to a detector (not shown).

All the mirrors 1, 5, 7, . . . , N are flat and parallel to one another. If the sample 3 is mounted parallel to the mirrors, the Faraday rotation multiplication effect will be enhanced by multiple internal reflections within the sample 3, and reflections off the front and back surfaces of the sample 3 will not be lost.

Alternatively, the sample 3 can be shaped as a wedge or mounted at an angle within the sample chamber 10. However, for a wedge shape or angled orientation, multiple internal reflections and reflections off the front and back surfaces of the sample 3 will escape the sample chamber 10 and be lost. The lost reflections are compensated for, along with absorption of the sample 3, by the optical amplifier chamber 6.

A conventional optical amplifier may be used for the optical amplifier chamber 6, which compensates for system losses, including absorption by the sample 3, transmission losses in the mirrors, and any escape of light from the sample chamber 10. The gain of the optical amplifier chamber 6 is adjusted to maintain operational intensity, while preventing over production of light energy in the optical amplifier chamber 6.

Ideally, the input mirror 1 allows light into the sample chamber 10 from the intense light source on the left, as viewed in FIG. 1, and no light out of the sample chamber 10 coming from the right toward mirror 1. In other words, ideally, mirror 1 is a "one-way mirror." If such an optical element is not available, mirror 1 should be the least transmissive mirror that will allow sufficient source light into the sample chamber 10 from the left, while minimizing leakage of light out of the sample chamber 10 by light that contacts mirror 1 from the right. Thus, the input mirror, mirror 1, has a very low transparency to allow a small percentage of the intense light source to enter the sample chamber 10, which, in turn, allows only this same very small percentage of sample chamber light to leak out of the sample chamber 10.

Mirror 5 operates as both the exit mirror of the sample chamber 10 and the entrance mirror to the optical amplifier chamber 6. The transparency of mirror 5 is set to a value that allows the maximum number of passes through the sample 3, while allowing a remaining intensity to pass through mirror 5 to the optical amplifier chamber 6, consistent with low noise amplification in the optical amplifier chamber 6. This is limited by absorption of the sample 3 for the wavelength of light used and losses due to reflections off the front and back surfaces of the sample 3 that may escape the sample chamber 10. The Faraday rotation is multiplied as much as possible by passing the beam through the sample 3 as many times as possible before passing through mirror 5 to the optical amplifier chamber 6. This mitigates as much as possible the insensitivity of the optical amplifier chamber 6 to polarization. Faraday rotation from the sample 3 may be very small and could be lost in the optical amplifier chamber 6 if it does not preserve polarization precisely.

Mirror 7 operates as the exit mirror of the optical amplifier chamber 6 and the entrance mirror to the multiplier chamber 12 following the optical amplifier chamber 6. The transparency of mirror 7 is adjusted to optimize the number of passes of the light beam through the optical amplifier chamber 6 that maintains operational intensity throughout the Faraday rotation amplifier 20 system, while preventing excessive build up of light energy in the optical amplifier chamber 6.

The light beam exits the optical amplifier chamber 6 through one of mirrors 5 or 7. The beam exiting through mirror 7 is reflected back to the optical amplifier chamber 6 by the multiplier chamber 12 that provides additional chambers beyond the optical amplifier chamber 6. The beam exiting the optical amplifier chamber 6 through mirror 5 passes back through the sample chamber 10 and the sample 3 to repeat the process.

The multiplier chamber 12 contains a series of sub-chambers formed by additional mirrors 8, 9, . . . , N following mirror 7 and the optical amplifier chamber 6. Mirrors 8, 9, . . . , N of the multiplier chamber 12 further multiply the output Faraday rotation by sending the light beam back through the optical amplifier chamber 6 and the sample 3. Faraday rotation multiplication takes place as light passes through the sample 3 in the sample chamber 10, with the light intensity being amplified in the optical amplifier chamber 6 to compensate for absorption and system losses. Each successive mirror 8, 9, . . . , N adds another multiplying factor to the Faraday rotation. The transparency of mirrors 1, 5, 7, . . . , N and the gain of the optical amplifier chamber 6 are optimized for maximum or optimum Faraday rotation multiplication. A potentially very large number of mirrors N can be added beyond the optical amplifier chamber 6 to provide a very large magnification factor for the Faraday or Voigt (described below) rotation signal. Each additional mirror added causes the light to be sent back through the series of chambers.

The number of passes through the sample 3 and, thus, the magnification factor for the rotation signal, is determined by the reflectivity and number of mirrors used. A sufficient number of mirrors are used such that enough passes are made through the sample 3 to provide a rotation signal that is strong enough to yield accurate measurements.

Figure 2:
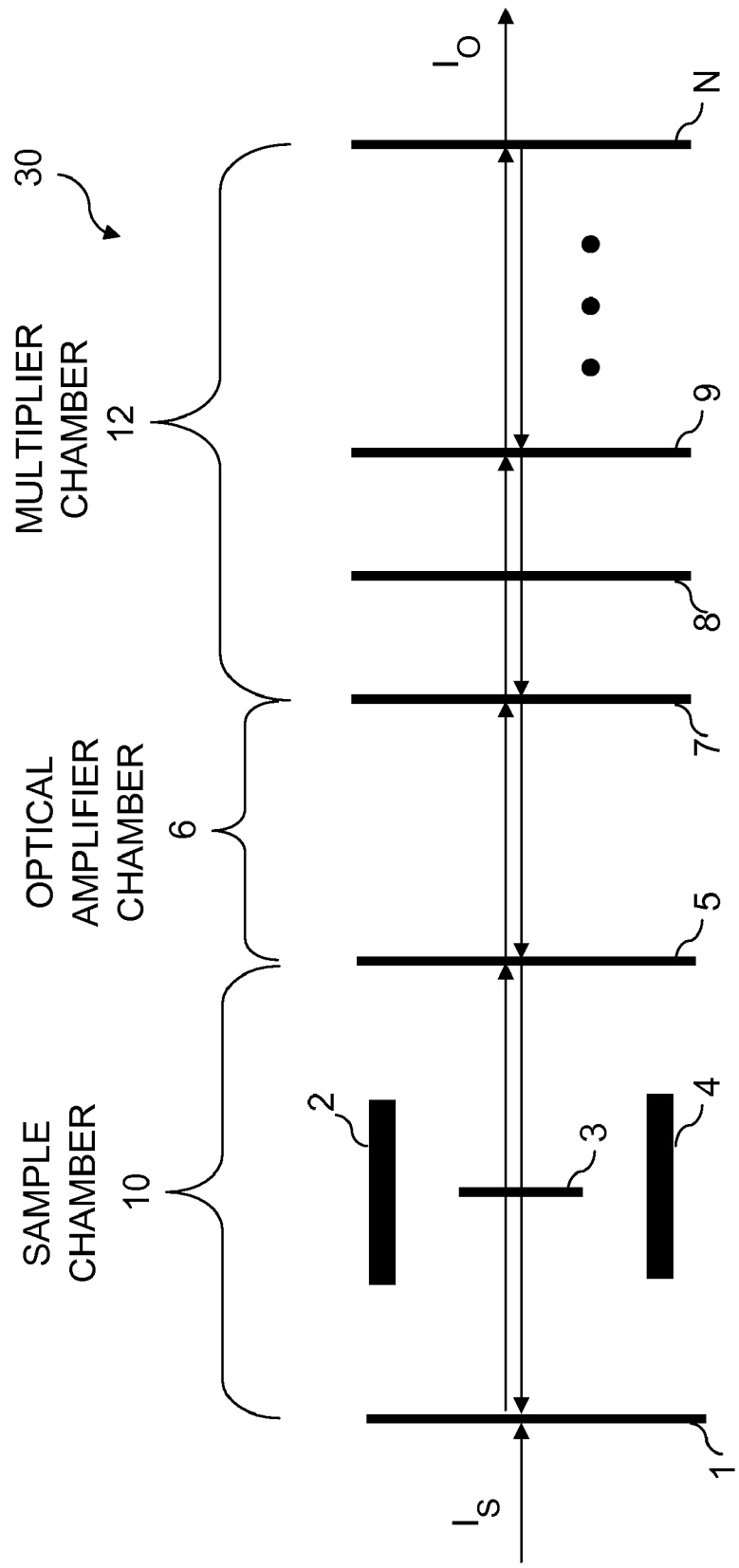
FIG. 2 shows a multiple pass Voigt rotation amplifier according to another embodiment of the present invention.

FIG. 2 shows a Voigt rotation amplifier 30 according to another embodiment of the present invention. In FIG. 2, the first pole 2 and the second pole 4 of the electromagnet are rotated 90° with respect to the light beam optical axis. Thus, in FIG. 2, the beam passes through only the sample 3 in the sample chamber 10 between mirrors 1 and 5 and not through the poles 2 and 4 of the electromagnet. The magnetic field lines are perpendicular to the light beam, and the Voigt rotation amplifier 30 amplifies the Voigt rotation signal through multiple passes as described above for the Faraday rotation signal.

In a further embodiment of the present invention, each one of the chambers is a Fabry-Perot chamber. The distance between each pair of mirrors is a multiple of half wavelengths of the light that is used. Mirrors 5, 7, . . . , N may be formed from layers of a transparent piezo-electric material that is coated on both sides with a metal or dielectric coating. The thickness of the layers may be finely adjusted by applying voltage to the layers. The optical amplifier chamber 6 may incorporate a gain material layer, such as an erbium dopant for light, from about 1.0 microns to about 1.5 microns. The beam diameter is approximately a few millimeters and, thus, the dimensions of each mirror are slightly larger than the beam diameter.

In still another embodiment of the present invention, the optical amplifier chamber 6 and all the sub-chambers of the multiplier chamber 12 have piezo-electric layers that incorporate metalized or dielectric layers for mirrors 5, 7, . . . , N, and all the layers in the optical amplifier chamber 6 and in the sub-chambers of the multiplier chamber 12 are doped with a gain material such as erbium. Thus, all chambers/sub-chambers following the sample chamber 10 have the same structure for easier manufacture.

In the above embodiments, two permanent magnets, rather than an electromagnet, may be used and are oriented with opposing poles on either side of the sample 3, with a hole drilled through for the Faraday configuration. No hole is needed for the Voigt configuration. Also, mirrors 5, 7, ..., N may be provided on an integrated optical chip (not shown) with a selector wheel to rotate chips with increasing numbers of mirrors into the optical path of the light to increase the rotation signal.

The present invention enables a very useful and well-established semiconductor characterization technique to be applied to even very thin films that are now common in modern semiconductor devices. The present invention can be used in a variety of military and civilian applications, including the examination of mercury cadmium (HgCdTe), indium antinomide (InSb), and gallium arsenide (GaAs) thin films used in infrared detectors/sensors (e.g., for missiles, aircraft, and ground vehicles) and focal plane arrays. Additional uses include characterizing the electron gas at the AlGaN/GaN interface in wafers used to grow gallium nitride (GaN) based transistors. The present invention can be used, generally, to multiply the Faraday or Voigt rotation in any material with low absorption loss to the wavelength of light used. Generally, Faraday and Voigt rotations are useful in screening for carrier concentration and/or effective mass in semiconducting materials.

Although a few embodiments of the present invention have been shown and described, it will be appreciated by those skilled in the art that changes may be made in these embodiments without departing from the principles and spirit of the invention, the scope of which is defined in the appended claims and their equivalents.

What is claimed is:

1. A multiple pass light rotation amplifier, comprising:
a sample chamber defined by a first mirror and a second mirror and containing a sample surrounded by a magnetic field generator that creates a magnetic field around and through the sample;
a light source supplying light to the sample chamber through the first mirror, the light reflecting a plurality of times between the first mirror and the second mirror, and the light undergoing cumulative rotation of a plane of polarization of the light with each pass of the light through the sample;
an optical amplifier chamber amplifying the light passing therethrough and being defined by the second mirror and a third mirror, the light reflecting a plurality of times between the second mirror and the third mirror; and
one or more additional chambers beyond the optical amplifier chamber,
wherein the sample chamber transmits the light to the optical amplifier chamber, the optical amplifier chamber transmits the light to a first one of the additional chambers and transmits the light back to the sample where the light undergoes further rotation, and each one of the additional chambers transmits the light to a next one of the additional chambers and transmits the light back to a preceding one of the additional chambers, the first one of the additional chambers transmitting the light back to the optical amplifier chamber and a last one of the additional chambers outputting a rotation signal.

2. The rotation amplifier of claim 1, wherein each additional chamber is adjacent to a preceding chamber and is defined on one end by a mirror defining the preceding chamber and on another end by an additional mirror.

3. The rotation amplifier of claim 1, wherein the sample has a first surface facing the first mirror and a second surface facing the second mirror, the light being reflected a plurality of times between the first mirror and the first surface and between the second mirror and the second surface and inside the sample between the first surface and the second surface, the light entering the first surface by reflection off the first mirror and by light passing through the first mirror from the light source, and the light entering the second surface by reflection off the second mirror and by light passing through the second mirror from the optical amplifier chamber, each passage of the light through the sample further accumulating the rotation of the light.

4. The rotation amplifier of claim 1, wherein the second mirror transmits a portion of the light within the sample chamber to the optical amplifier chamber and reflects a remaining portion of the light back to the sample, the remaining portion of the light traveling back to the sample being partially transmitted through the sample to further accumulate the rotation of the light, exiting the sample, and then being reflected back to the sample by the first mirror to further accumulate the rotation of the light.

5. The rotation amplifier of claim 1, wherein the optical amplifier chamber compensates for absorption of the sample and transmission losses from the apparatus, and the amplification of the light and the number of passes of the light within the optical amplifier chamber are determined by an optical gain of the optical amplifier chamber and the transparency of the second mirror and the third mirror.

6. The rotation amplifier of claim 1, wherein the first mirror is a low transparency mirror that allows the light to enter the sample chamber from the light source, while preventing the light within the sample chamber from escaping.

7. The rotation amplifier of claim 1, wherein the second mirror is a partially transparent mirror that allows a maximum number of passes of the light through the sample, according to an absorption of the sample and a wavelength of the light, before the light is transmitted to the optical amplifier chamber, to mitigate insensitivity of the optical amplifier chamber to polarization of the light.

8. The rotation amplifier of claim 1, wherein the light source is a laser emitting linearly polarized light.

9. The rotation amplifier of claim 1, wherein the sample is a thin film semiconductor material.

10. The rotation amplifier of claim 1, wherein the sample is selected from the group consisting of mercury cadmium (HgCdTe), indium antinomide (InSb), gallium arsenide (GaAs), and AlGaN/GaN.

11. The rotation amplifier of claim 1, wherein the magnetic field generator is an electromagnet.

12. The rotation amplifier of claim 11, wherein the magnet has a first pole and a second pole, the first pole and the second pole being parallel to an optical axis of the light and both having a hole to allow the light to pass therethrough, the light passing through the first pole between the first mirror and the sample, and the light passing through the second pole between the sample and the second mirror, the light passing through the sample undergoing Faraday rotation.

13. The rotation amplifier of claim 11, wherein the magnet has a first pole and a second pole, the first pole and the second pole being perpendicular to an optical axis of the light, the light passing through the sample undergoing Voigt rotation.

14. The rotation amplifier of claim 1, wherein the sample, the first mirror, and the second mirror are parallel to one another and perpendicular to an optical axis of the light.

15. The rotation amplifier of claim 1, wherein the first mirror is parallel to the second mirror and at least one of the first surface and the second surface of the sample is positioned at an angle to the first mirror and to the second mirror.

16. A method of amplifying rotation of a plane of polarization of light for a sample within a sample chamber, the sample chamber being adjacent to an optical amplifier chamber, and the optical amplifier chamber being adjacent to one or more additional chambers, the method comprising:
transmitting light into the sample chamber and through the sample having a magnetic field applied thereto, the light reflecting within the sample chamber and the sample to accumulate rotation of a plane of polarization of the light;
transmitting the light from the sample chamber to the optical amplifier chamber to amplify the intensity of the light passing therethrough, and transmitting the light to a first one of the additional chambers and reflecting the light back to the sample where the light undergoes further rotation;
transmitting the light from the optical amplifier chamber to the additional chambers, each one of the additional chambers transmitting the light to a next one of the additional chambers and reflecting the light back to a previous one of the additional chambers, the first one of the additional chambers reflecting the light back to the optical amplifier.

17. The method of claim 16, further comprising bounding the optical amplifier chamber by a pair of mirrors and compensating, within the optical amplifier chamber, for absorption of the sample and transmission losses, the amplification of the light intensity and the number of passes of the light within the optical amplifier chamber being determined by an optical gain of the optical amplifier chamber and the transparency of the pair of mirrors.

18. The method of claim 16, further comprising providing a light source to supply the light and providing a first mirror and a second mirror to bound the sample chamber, the first mirror receiving the light from the light source and having a low transparency to allow the light to enter the sample chamber from the light source, while preventing the light within the sample chamber from escaping, and the second mirror allowing a maximum number of passes of the light through the sample, according to an absorption of the sample and a wavelength of the light, before the light is transmitted to the optical amplifier chamber, to mitigate insensitivity of the optical amplifier chamber to polarization of the light.

19. The method of claim 16, wherein transmitting the light through the sample comprises transmitting the light through a thin film semiconductor material.

20. A multiple pass light rotation amplifier, comprising:
a sample chamber defined by a first mirror and a second mirror and containing a sample surrounded by a magnetic field generator that creates a magnetic field around and through the sample;
a light source supplying light to the sample chamber through the first mirror, the light reflecting a plurality of times between the first mirror and the second mirror, and the light undergoing cumulative rotation of a plane of polarization of the light with each pass of the light through the sample;
an optical amplifier chamber adjacent to the sample chamber, the optical amplifier amplifying the light passing therethrough and being defined by the second mirror and a third mirror, the light reflecting a plurality of times between the second mirror and the third mirror; and
a multiplier chamber adjacent to the optical amplifier chamber,
wherein the sample chamber transmits the light to the optical amplifier chamber, the optical amplifier chamber transmits the light to the multiplier chamber and reflects the light back to the sample where the light undergoes further rotation, and the multiplier chamber reflects the light back to the optical amplifier chamber and outputs a rotation signal.

21. The multiple pass light rotation amplifier of claim 20, wherein the multiplier chamber comprises one or more sub-chambers defined by additional mirrors.

22. A multiple pass light rotation amplifier, comprising:
a sample chamber receiving light and containing a sample, the light reflecting a plurality of times within the sample and the sample chamber and undergoing cumulative Faraday rotation with each pass of the light through the sample;
an optical amplifier chamber adjacent to the sample chamber to amplify the light passing therethrough; and
a multiplier chamber adjacent to the optical amplifier chamber, the multiplier chamber receiving the light from the optical amplifier chamber, outputting a rotation signal, and reflecting the light back to the optical amplifier chamber, and the optical amplifier chamber reflecting the light received from the sample chamber and the multiplier chamber back to the sample chamber, where the light undergoes further rotation.

23. The multiple pass light rotation amplifier of claim 22, wherein the multiplier chamber comprises one or more sub-chambers that repeatedly reflect the light back toward the sample.

* * * * *